United States Patent [19]
Blake, III

[11] Patent Number: 5,242,412
[45] Date of Patent: Sep. 7, 1993

[54] TROCAR TUBE SUBASSEMBLY HAVING SEALING RING AND DUCKBILL SEALING TUBE HAVING PLANAR, TRUNCATE, DIVERGING SEALING BILLS

[76] Inventor: Joseph W. Blake, III, 9 Taylor Ave., Norwalk, Conn. 06854

[21] Appl. No.: 822,719
[22] Filed: Jan. 21, 1992
[51] Int. Cl.⁵ ............................................. A61M 5/178
[52] U.S. Cl. ..................................................... 604/167
[58] Field of Search ................ 604/167, 169, 256, 164

[56] References Cited

U.S. PATENT DOCUMENTS

| | | | |
|---|---|---|---|
| 3,875,938 | 4/1975 | Mellor | 604/169 X |
| 4,106,491 | 8/1978 | Guerra | 604/169 X |
| 4,240,411 | 12/1980 | Hosono | 604/167 X |
| 4,946,133 | 8/1990 | Johnson et al. | 604/256 X |

FOREIGN PATENT DOCUMENTS 3042229  5/1982  Fed. Rep. of Germany ...... 604/167

Primary Examiner—John J. Wilson
Assistant Examiner—Jeffrey A. Smith
Attorney, Agent, or Firm—Patrick J. Walsh

[57] ABSTRACT

A trocar assembly of trocar tube and trocar obturator includes a seal comprising a sealing ring and a sealing valve positioned in the trocar tube housing in concentric relationship with the trocar obturator and its protective shield for sealing (i) the trocar obturator when interfitted with the tube, (ii) sealing endoscopic instruments when deployed through the tube in performing medical procedures, and (iii) the trocar tube remaining alone in a body cavity.

3 Claims, 2 Drawing Sheets

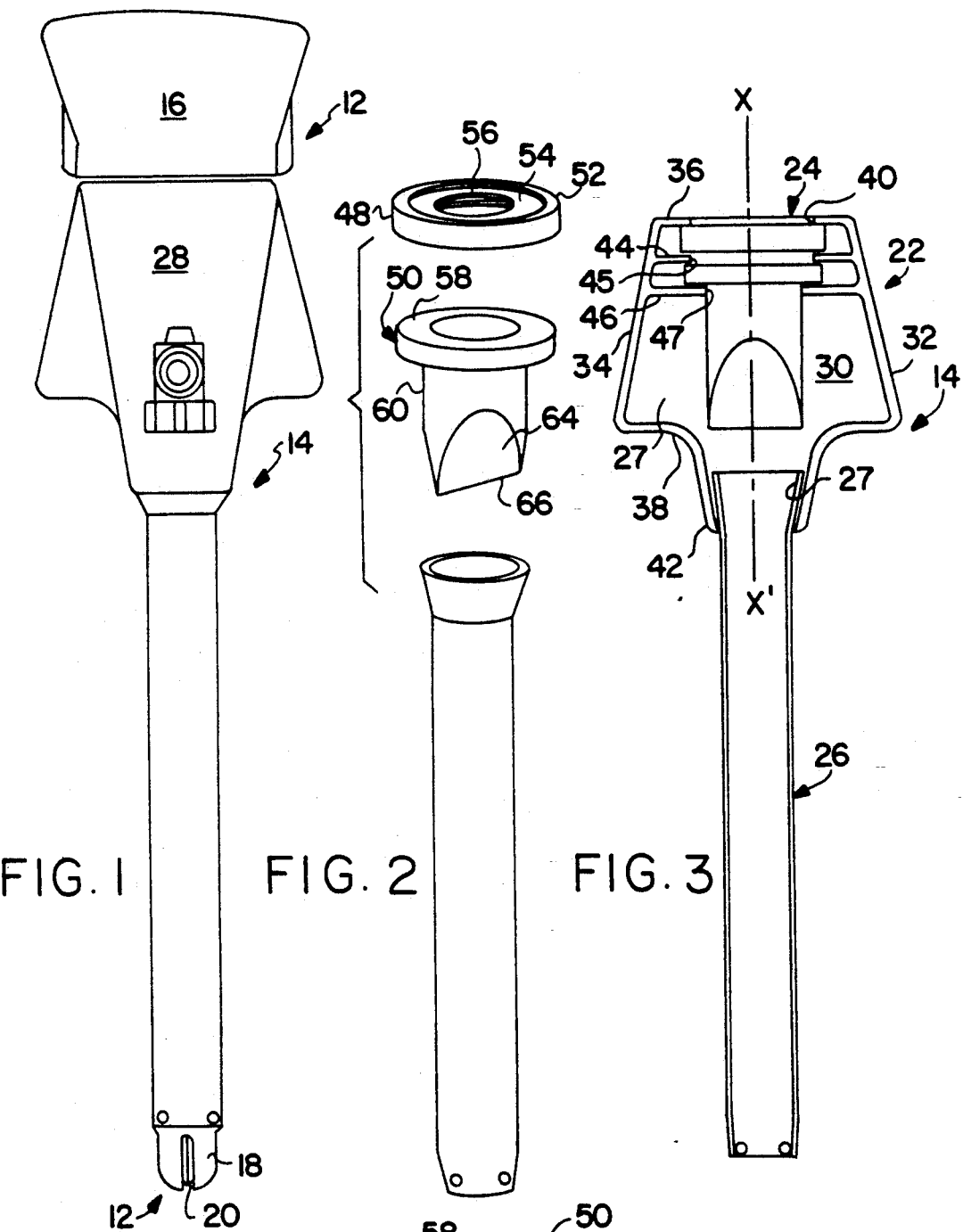

TROCAR TUBE SUBASSEMBLY HAVING SEALING RING AND DUCKBILL SEALING TUBE HAVING PLANAR, TRUNCATE, DIVERGING SEALING BILLS

BACKGROUND OF THE INVENTION

The present invention relates to surgical instruments and particularly to an improved seal arrangement for a trocar tube.

A conventional trocar assembly comprises two basic interfitting, separable components: a trocar obturator subassembly and a trocar tube subassembly. The trocar obturator subassembly includes a supporting head with an elongate obturator having a cutting tip and a protective shield. The trocar tube includes a head and a depending tube together with a sealing arrangement within the head for closing and sealing the tube when it is in position during surgery. The assembly includes the trocar obturator and protective shield interfitting the trocar tube with the cutting tip projecting from the end of the tube and being covered by the protective shield.

In ordinary use the trocar assembly penetrates a body cavity and the trocar obturator subassembly is withdrawn leaving the trocar tube in place for introducing other instruments into the body according to the requirements of a particular medical procedure. The trocar tube is provided with a sealing arrangement to close the tube in order to maintain the gas pressure within the body cavity as required for the medical procedure.

Conventional sealing arrangements such as disclosed in U.S. Pat. Nos. 4,931,042 and 5,030,206 include a swinging flapper valve located in the head portion of the trocar tube subassembly which swings closed when the obturator and protective shield are removed. The flapper valve is spring loaded and closes against a sealing ring or grommet fitted around the head access opening. When an instrument is inserted into the trocar tube the flapper valve is either pushed aside by the instrument or by an external lever fitted to the side of the head portion. The flapper valve arrangement although providing a suitable seal is a rather cumbersome arrangement.

U.S. Pat. No. 4,972,827 utilizes a slide valve fitted within a chamber forming part of the trocar tube. The slide valve and chamber are oriented perpendicular to the trocar tube axis and when the trocar obturator is removed, the slide valve is pushed laterally by a spring to cross over the tube axis and seal the tube. This arrangement is also cumbersome and requires manual operation to align the opening through the slide valve with the trocar obturator or other instrument required for a medical procedure.

SUMMARY OF THE INVENTION

The present invention comprises an improved seal for a trocar. According to the invention a unitary self sealing valve member is placed in the trocar tube head component in longitudinal alignment with the the trocar tube and with the obturator and protective shield. The valve comprises a supple rubber or plastic of tubular construction with an integral retaining collar at one end for positioning in the head. The other end of the valve includes valve walls converging to form sealing lips for closing the valve. The valve readily allows entry and exit of instruments such as the obturator and protective shield, surgical scissors, and so forth. When an instrument is withdrawn, the gas pressure existing in a body cavity acts on the valve walls pressing the lips together and effectively sealing the trocar tube.

A sealing ring is located at the entrance to the trocar tube head and provides for sealing of the tube interior and for maintaining body cavity gas pressure when an instrument occupies the tube. The sealing ring and the self-sealing valve may be of unitary construction and positioned as a unit in longitudinal alignment within the trocar tube head. In this way a single sealing unit assures maintenance of gas pressure within the trocar tube when an instrument is in place in the tube and after it has been removed. Moreover, the sealing unit minimizes the loss of gas pressure while an instrument enters or leaves the trocar tube. The sealing ring and sealing valve act sequentially so that when an instrument enters the trocar tube the ring forms a seal about the instrument before the instrument opens and passes through the valve, and when an instrument exits the trocar tube the valve closes and forms a seal within the trocar tube before the instrument passes out of the ring.

OBJECTS OF THE INVENTION

It is an object of the invention to provide a trocar with an improved seal.

It is an object of the invention to provide a trocar with a unitary seal comprising a single part.

It is a further object of the invention to provide a seal for a trocar which is easy to install, reliable and self sealing.

Another object of the invention is to provide a seal for a trocar tube comprising a seal ring for sealing gas pressure within the tube when an instrument extends through the tube, and a self sealing valve for maintaining gas pressure when the instrument is removed from the tube.

It is a further object of the invention to provide for a trocar a seal of supple material which is self-sealing when the trocar tube is idle and which aids in sealing the periphery of a surgical instrument occupying the trocar tube.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which:

FIG. 1 is a front elevation view of a trocar according to the invention.

FIG. 2 is a front elevation view in section of the trocar tube subassembly according to the invention.

FIG. 3 is an exploded perspective view of individual components of the subassembly of FIG. 2.

FIG. 4 is a fragmentary perspective view of the sealing element of FIGS. 2 and 3 in sealing engagement with a surgical instrument.

DETAILED DESCRIPTION OF THE INVENTION

Figure 5:
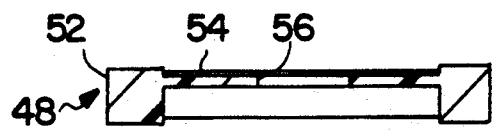
FIGS. 5 and 6 are respectively longitudinal sectional views of a preferred embodiment of a sealing ring and sealing valve according to the invention.

Referring now to the drawing, a trocar 10 according to the invention comprises a trocar obturator subassembly 12 and a trocar tube subassembly 14. The trocar as shown in FIG. 1 is the interfitting obturator and tube components prior to actual use of the instrument. The obturator subassembly includes an upper housing 16 which serves as a handle for carrying and manipulating the obturator. The upper housing also includes a mechanism (not shown) for deploying a protective shield 18 about the cutting tip 20 after the tip penetrates a body cavity. The protective shield and the cutting tip of the obturator are shown in FIG. 1 projecting from the lower end of the trocar tube 14.

The trocar tube subassembly 14 comprises a housing 22, a seal 24 and a tube 26. The housing is a rigid plastic shell having an interior chamber 27 defined by front 28, rear 30, side 32, 34, top 36 and bottom 38 walls. There is a central passage x—x' through the housing defined by an opening 40 in the top wall and a flared tubular channel 42 emerging from the bottom wall. In a preferred arrangement, the housing includes interior middle 44 and lower 46 transverse supporting walls for positioning sealing members 24 in the central passage. The trocar tube 26 consists of an aluminum tube with a flared head portion 29 which fits into and is supported by the tubular channel 42. In the assembled trocar, the obturator and its protective shield occupy the central passage and the interior of the tube.

In accordance with the invention, a sealing ring 48 and a sealing valve 50 provide for sealing the trocar in its various modes of usage. The sealing ring is positioned at the entrance opening 40 of the top wall of the housing and encompasses the central passage x—x'. The ring comprises a cylindrical rim or flange 52 having a radially extending annular sealing web 54 with an inner diameter less than the outer diameter of the protective shield 18 of the obturator. The inner edge 56 of the sealing web forms a seal about the shield surface. The sealing web is sufficiently thin in cross-section to deflect downwardly and upwardly as the shield enters and leaves the trocar tube. The sealing ring therefore establishes a gas pressure seal about the shield when the trocar assembly is in position during a surgical procedure. In a preferred embodiment, the tube housing is provided with a middle transverse wall 44 having an opening 45 aligned with the entrance opening 40 and encompassing the central passage. The middle transverse wall cooperates with the top wall of the housing for positioning the sealing ring in assembled position.

Figure 6:
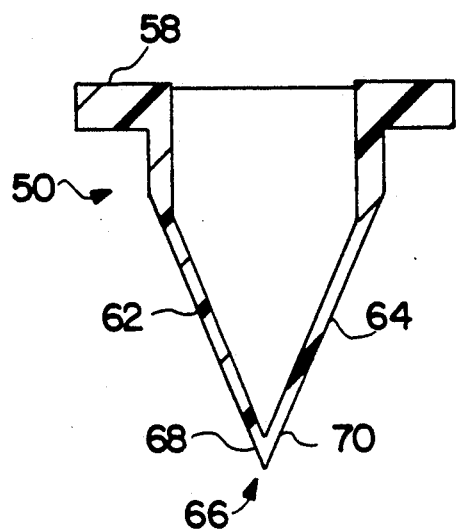

The sealing valve 50 comprises an end flange 58 and an integral depending tube 60 formed of a supple rubber or plastic. The sealing valve is normally positioned in the trocar tube housing between the middle 44 and lower 46 transverse walls through opening 47 and encompasses the central passage. As shown in FIGS. 3, 4 and 6, the sealing valve includes a generally cylindrical body or tube 60 with integral, planar, truncate side walls or sealing flaps 62, 64 converging at an apex 66 and there defining diametric sealing lips 68, 70. The sealing flaps come together forming sealing lips along a seal tube diameter coincident with apex 66 and lying in the plane of each sidewall. The sealing flaps preferably have a wall thickness significantly less than tube wall thickness for ease of flexing of the flaps as they form a seal. The thicker tube walls support the flaps in various sealing configurations shown in FIGS. 2 and 4. The tube walls also restore the sealing flaps to the position of FIG. 3 after withdrawal of the surgical instrument of FIG. 4. If desired the tube walls and the truncate walls may have substantially the same wall thickness.

FIG. 2 illustrates the sealing valve in position sealing body cavity overpressure within chamber 27 when neither obturator nor endoscopic instrument occupies the trocar tube. FIG. 4 on the other hand illustrates an endoscopic instrument such as surgical scissors 69 occupying the sealing valve with sealing lips 68 and 70 encompassing instrument tube 71. The sealing ring 48 of FIG. 3 also encompasses the instrument tube 71 forming a seal with sealing web 54 and there sealing body cavity overpressure within chamber 27. This arrangement provides for entry and sealing of the obturator and endoscopic instruments through the trocar tube in the course of medical procedures.

Figure 8:
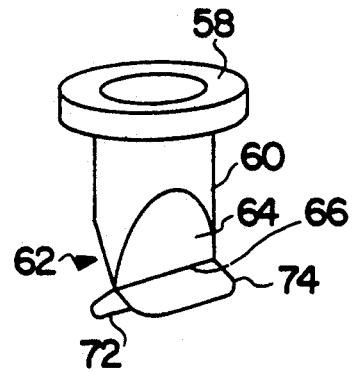

In a modified form of the invention shown in FIG. 8, the sealing flaps 62, 64 extend beyond sealing apex 66 and terminate in diverging lip extensions or bills 72, 74 which prevent inversion or inward collapse of the sealing flaps when an obturator is withdrawn from the trocar tube. Inversion of the sealing flaps could result in failure of the seal and loss of body cavity gas pressure. The bills assure correct positioning of the sealing lips after obturator removal.

It will be noted further in FIG. 2 that the flange portions 52, 58 of the sealing ring and the sealing valve form seals around openings 40, 45, and 47 with respective mating surfaces of the top, middle and lower transverse walls of the tube housing. These seals prevent escape of body cavity gas pressure from the interior of the housing along the outer surfaces of the ring and valve flanges.

Figure 7:
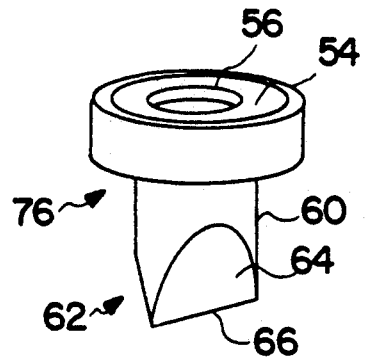
FIGS. 7 and 8 are perspective views of a modified sealing valves for a trocar tube subassembly.

If desired, the sealing ring and sealing valve (FIG. 7) may be formed as a unit 76 with their flanges joined or combined to provide a tubular sealing enclosure for the entrance to the tube housing encompassing the central passage. In this form the middle transverse wall may be omitted from the trocar tube housing.

In operation, the trocar is placed in initial position in a body cavity with the tip covered by the shield as shown in FIG. 1. In this position, the seals maintain gas pressure within the body cavity. The seal ring encompasses the trocar shield with the sealing web in peripheral engagement with the shield surface. Additionally, the valve sealing lips engage the shield surface and establish a secondary seal. Insufflating gas introduced into the tube housing tends to press the sealing lips against the shield as an aid in maintaining gas pressure within the body cavity. Substantially similar sealing action occurs when a surgical instrument as shown in FIG. 4 is deployed through the valve.

When instruments are withdrawn from the trocar tube and the tube remains in place in a body cavity, the sealing lips provide a seal for gas pressure in the cavity. The interior of the sealing valve along passage x—x' is at atmospheric pressure while the valve exterior within the housing chamber is exposed to the overpressure of the body cavity. The pressure differential squeezes the lips together to form the seal. The valve walls resist deflection under the pressure differential while the sealing flaps having thinner walls in a preferred arrangement engage in lip to lip sealing relationship. In this way a single sealing unit assures maintenance of gas pressure within the trocar tube when an instrument is in place and after it has been removed. Moreover, the sealing unit minimizes the loss of gas pressure while an instrument enters or leaves the trocar tube. The sealing ring and valve act sequentially so when an instrument enters the trocar the ring forms a seal about the instrument before the instrument opens and passes through the valve. When an instrument exits the trocar tube the valve closes and forms a seal in the trocar chamber before the instrument passes through the ring.

I claim:

1. A trocar tube subassembly for receiving a trocar obturator subassembly having a protective shield, the trocar tube subassembly comprising a housing in the form of a hollow shell with aligned first and second openings in opposite sides of the housing defining a central passage therethrough, the first opening being in a top side of the shell, the second opening being in a bottom side and having a tube affixed thereto, the tube having an axis aligned with the central passage, first and second interior transverse supporting walls within the shell being spaced from each other and from the top side of the shell along the central passage, with each of the interior walls having an opening aligned with both of the shell openings and further defining the central passage, a sealing ring located in the space between said top side and said first interior wall with the upper and lower surfaces of the sealing ring in engagement, respectively, with the top and first interior walls, the sealing ring having a rim with a radially extending annular sealing web having an inner diameter less than an outer diameter of the trocar obturator subassembly protective shield so that the inner edge forms a seal about the protective shield, a sealing tube having a cylindrical portion extending along the central passage, the cylindrical portion of the sealing tube including integral, planar, truncate sealing flaps converging at an apex and there defining diametric sealing lips for sealing the interior of the shell when the trocar obturator subassembly is removed from the trocar tube subassembly, said sealing flaps extending beyond the apex and terminating in diverging bills which prevent inward collapse of the sealing flaps when an instrument is withdrawn from the trocar tube the sealing tube having a peripheral flange in engagement with the first and second interior walls for retaining the sealing tube in position along the central passage, and the sealing ring and the sealing tube cooperating to seal the interior of the trocar tube subassembly, respectively, when the trocar obturator subassembly is in place and when it is removed.

2. A trocar tube subassembly as defined in claim 1 in which the sealing tube is formed of supple material.

3. A trocar tube subassembly as defined in claim 1 in which the sealing flaps are thinner than the sealing tube cylindrical wall.

* * * * *